United States Patent [19]
Jensen et al.

[11] Patent Number: 5,843,087
[45] Date of Patent: Dec. 1, 1998

[54] SUTURE ANCHOR INSTALLATION TOOL

[75] Inventors: Kenneth L. Jensen, Providence; Mikael Roberts, Logan, both of Utah

[73] Assignee: Ethicon, Inc., Somerville, N.J.

[21] Appl. No.: 791,000

[22] Filed: Jan. 30, 1997

[51] Int. Cl.[6] .................................................. A61B 17/04
[52] U.S. Cl. ............................. 606/104; 606/72; 606/75; 606/232
[58] Field of Search ................................. 606/72–75, 104, 606/232

[56] References Cited

U.S. PATENT DOCUMENTS

| | | | |
|---|---|---|---|
| 4,898,156 | 2/1990 | Gatturna et al. | 606/72 |
| 5,002,550 | 3/1991 | Li | 606/232 |
| 5,192,303 | 3/1993 | Gatturna et al. | 606/232 |
| 5,520,696 | 5/1996 | Wenstorom, Jr. | 606/104 |

*Primary Examiner*—Gary Jackson
*Attorney, Agent, or Firm*—Pandiscio & Pandiscio

[57] ABSTRACT

A bone anchor installation tool for deploying a bone anchor in bone.

8 Claims, 15 Drawing Sheets

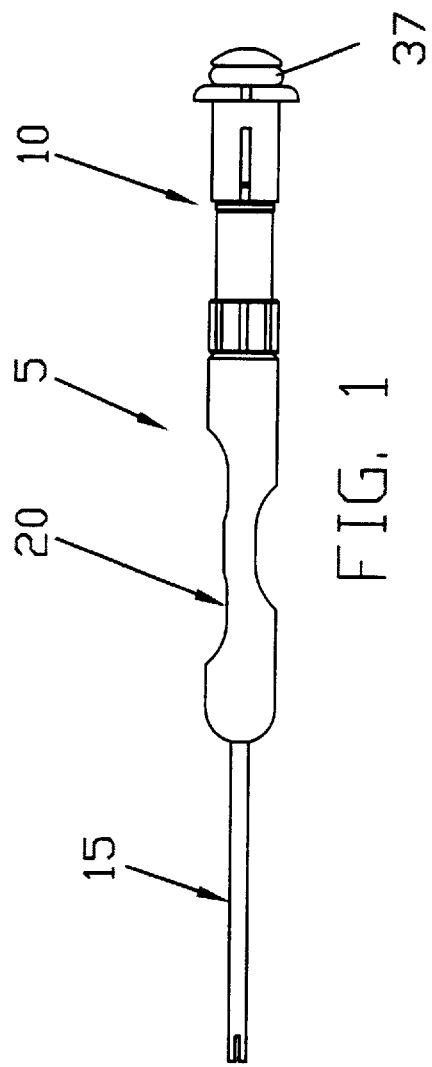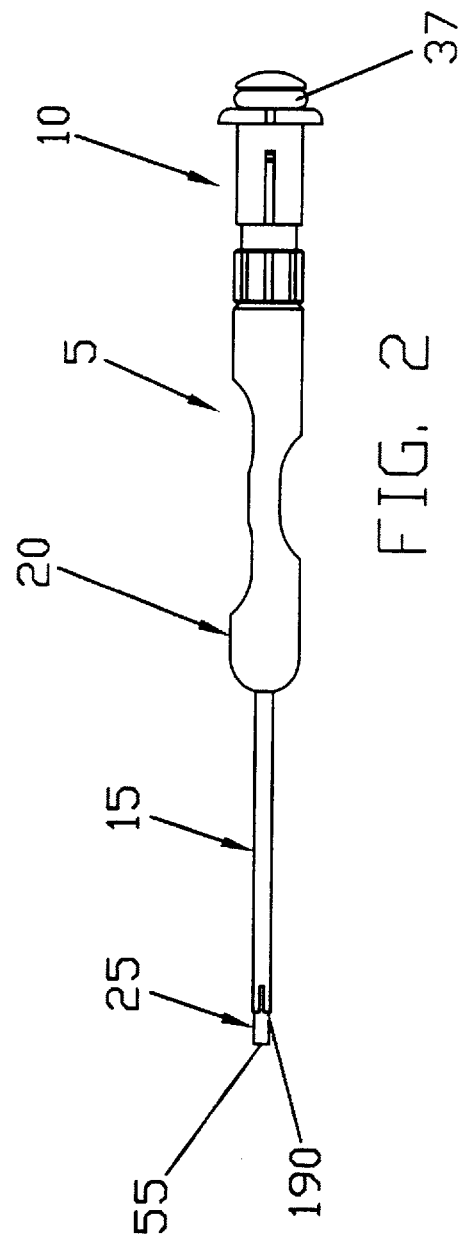

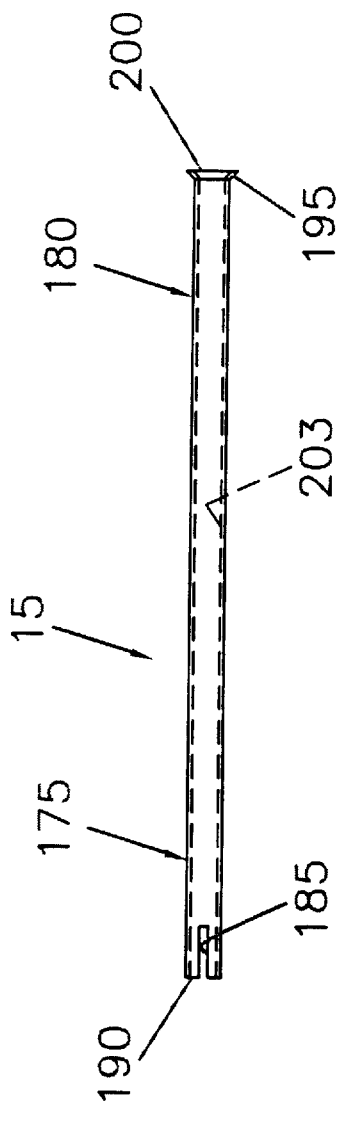
FIG. 4
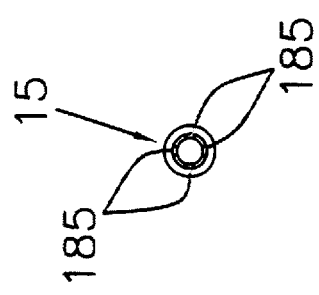
FIG. 5
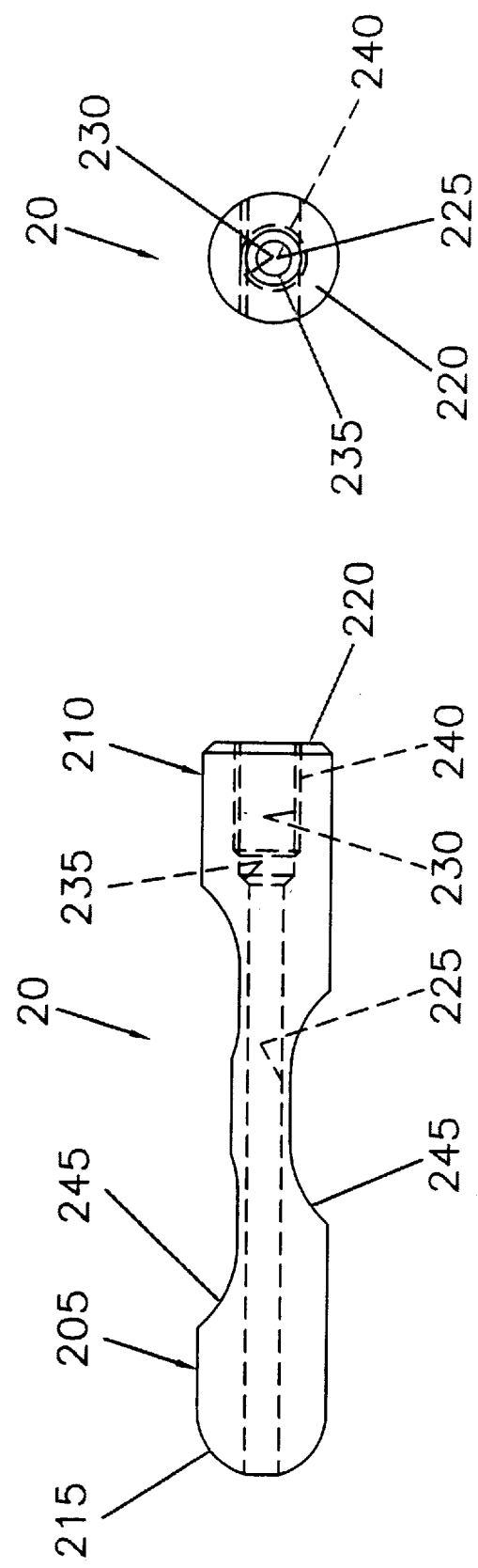
FIG. 7
FIG. 6

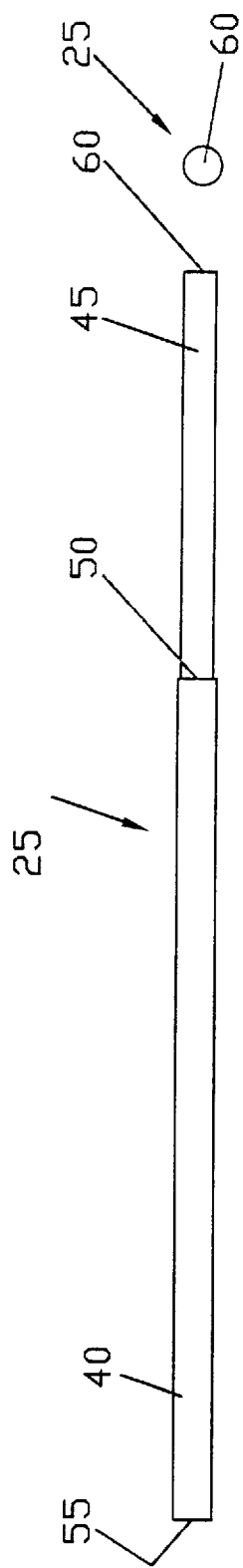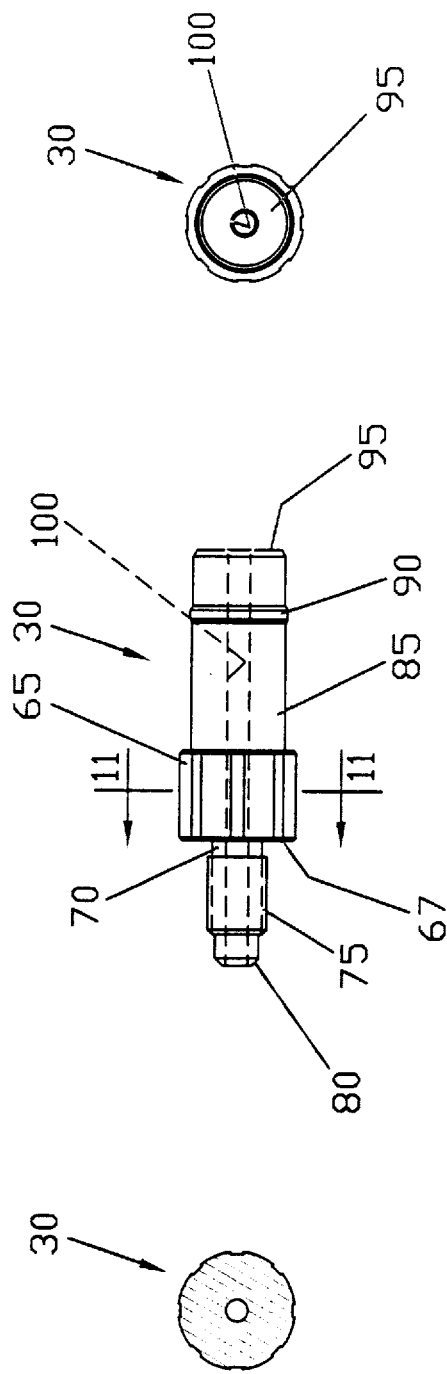

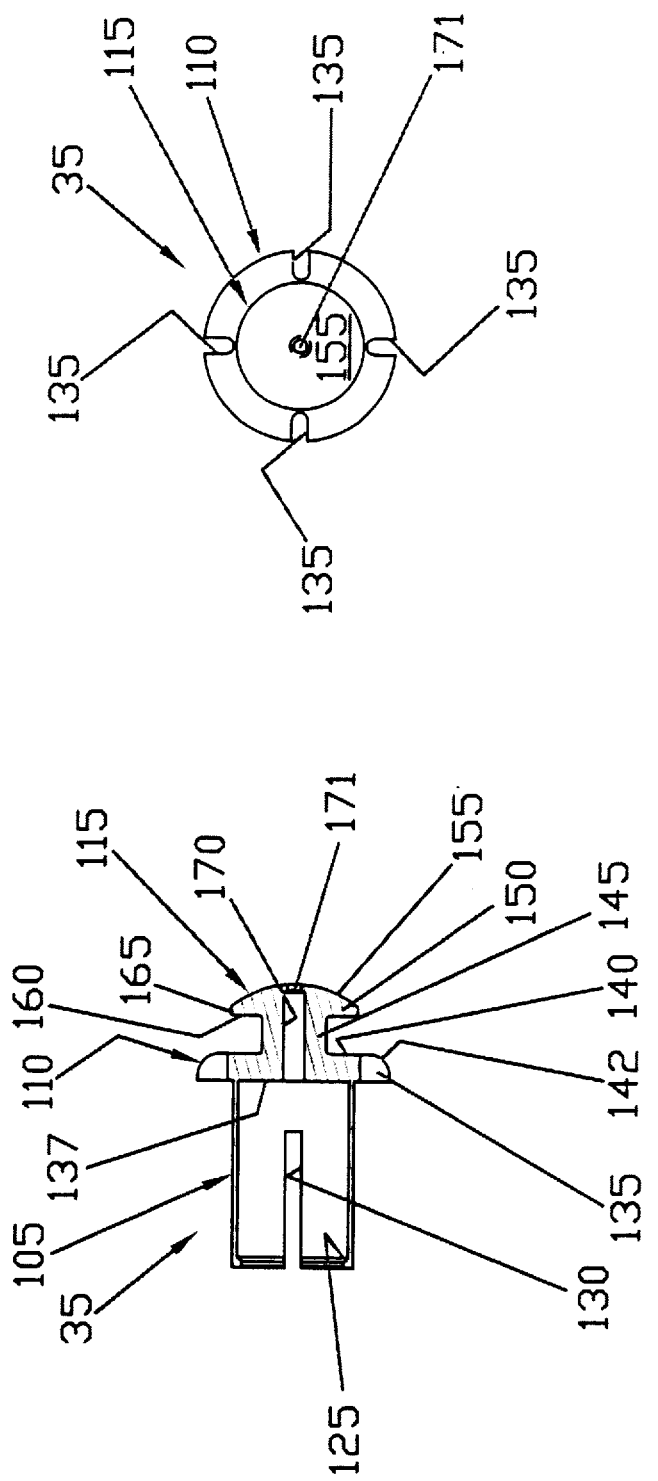

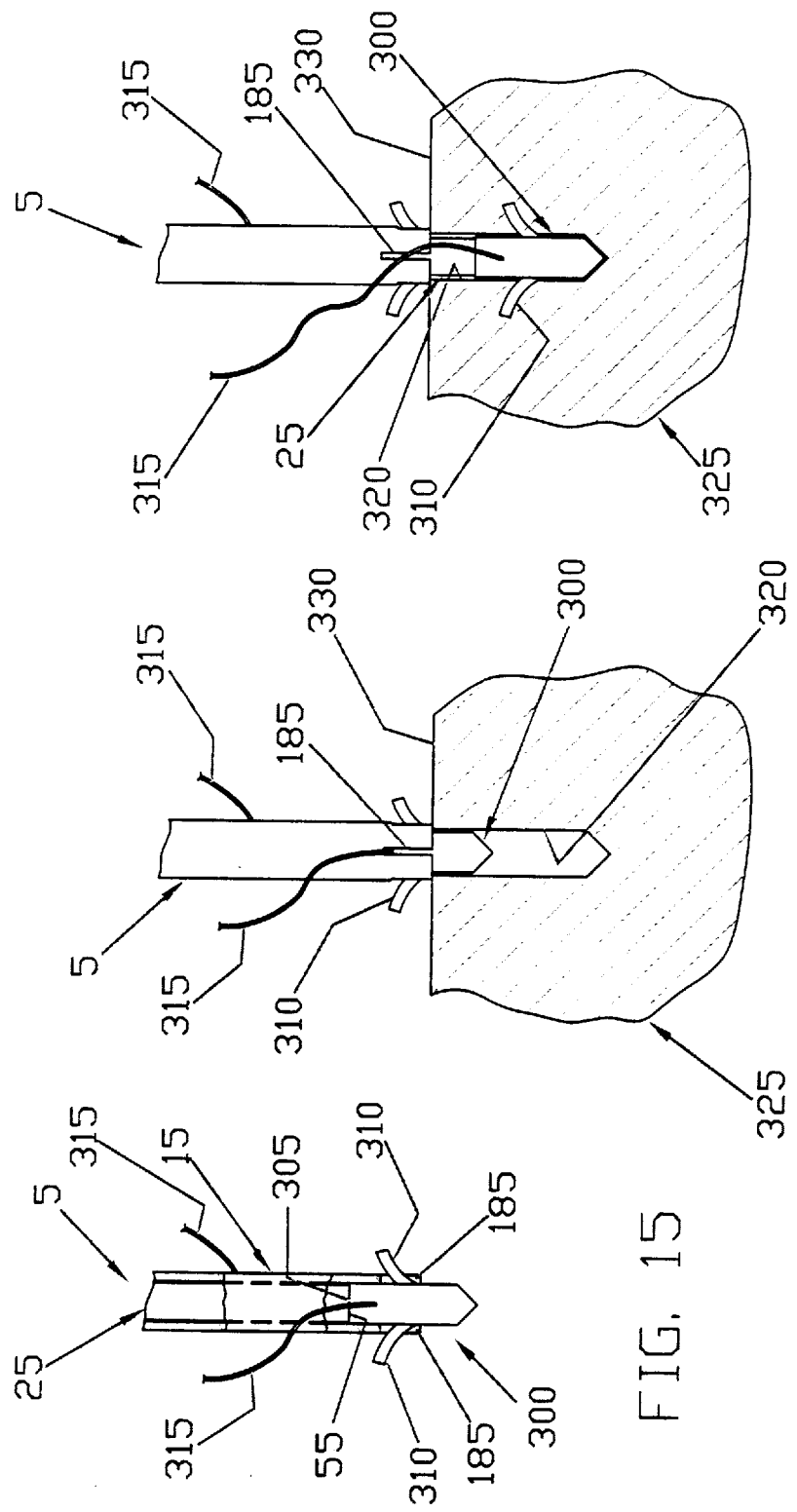

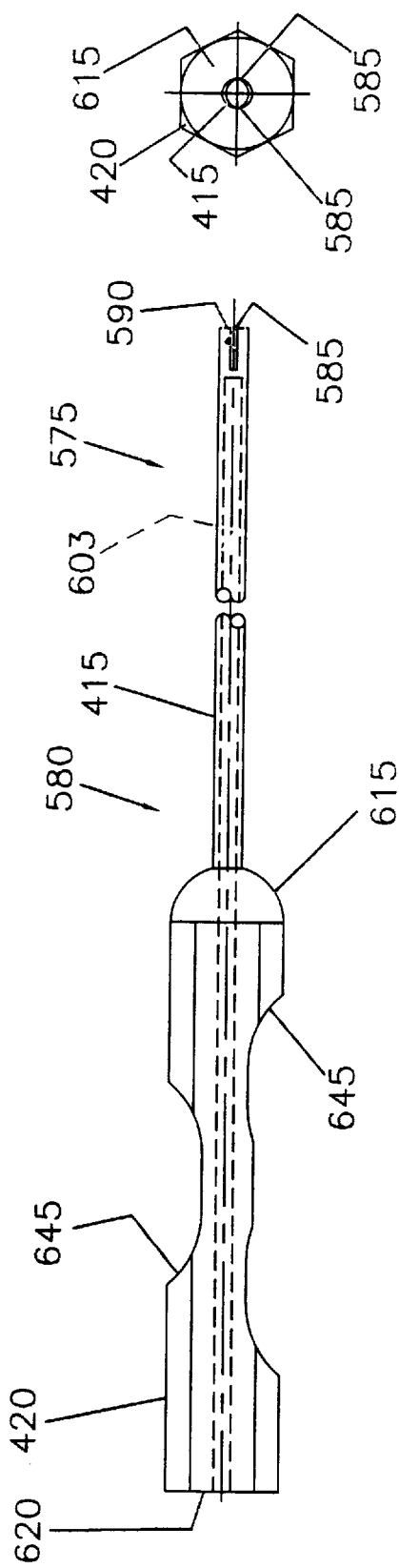

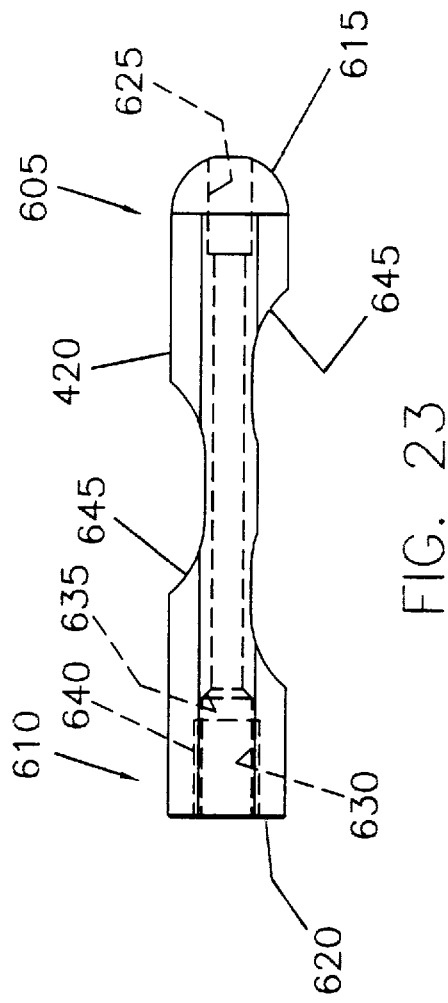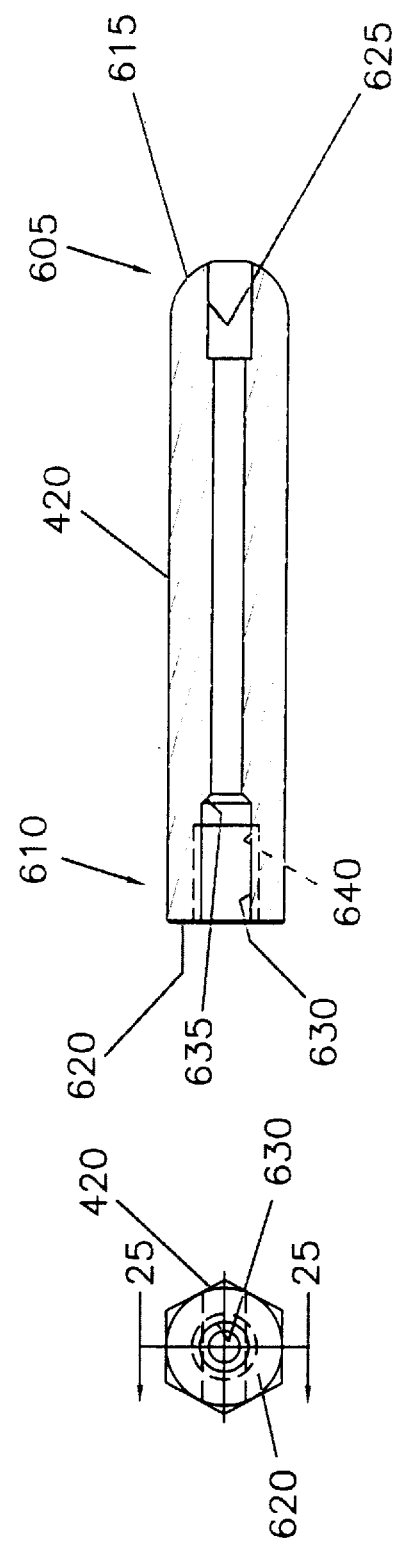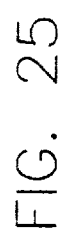

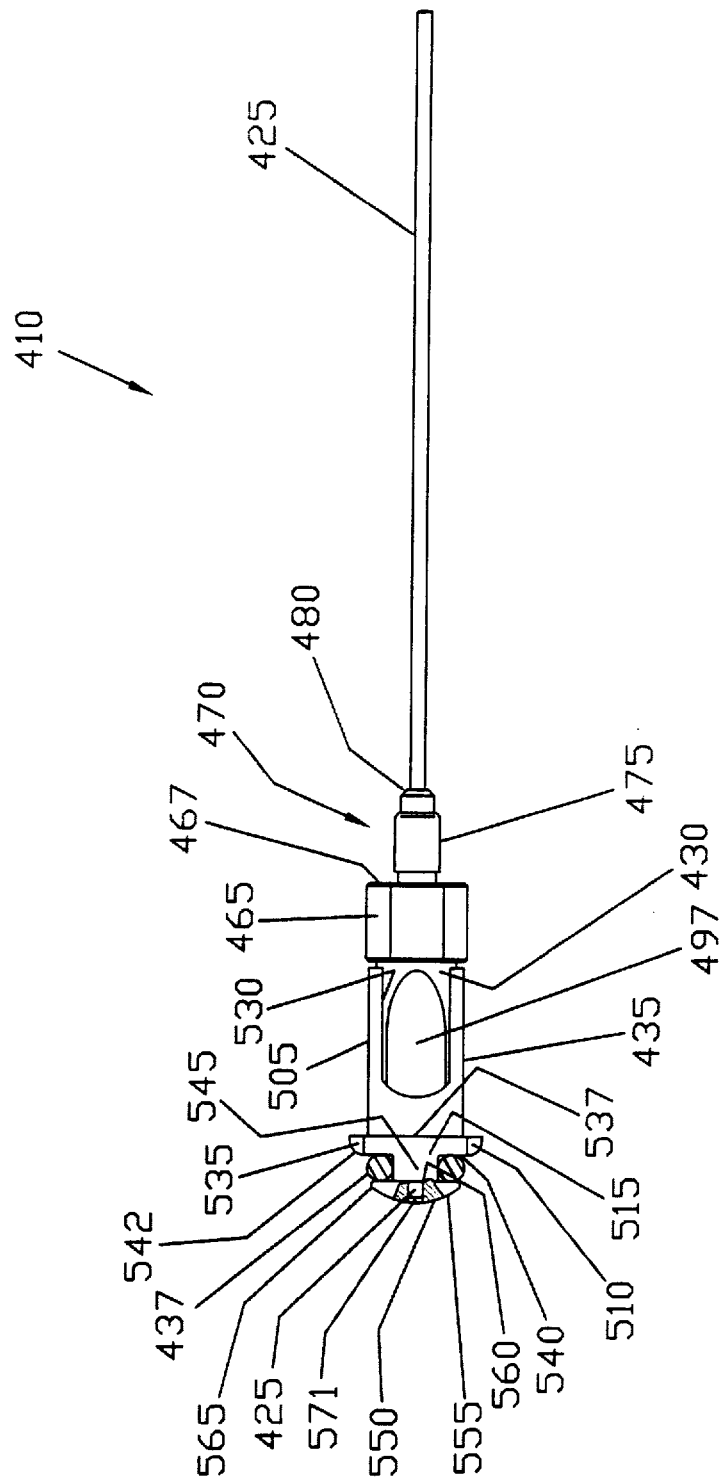

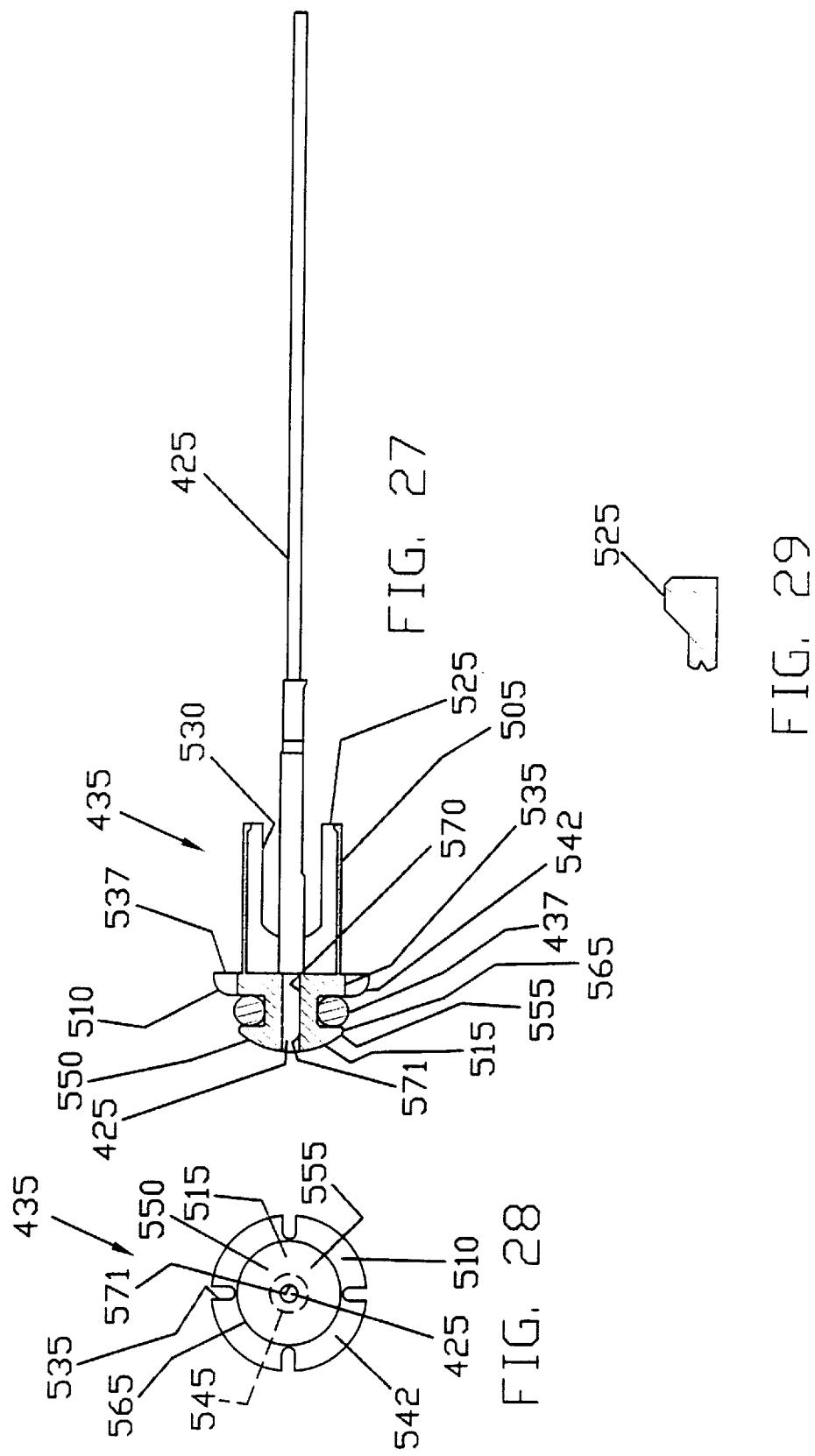

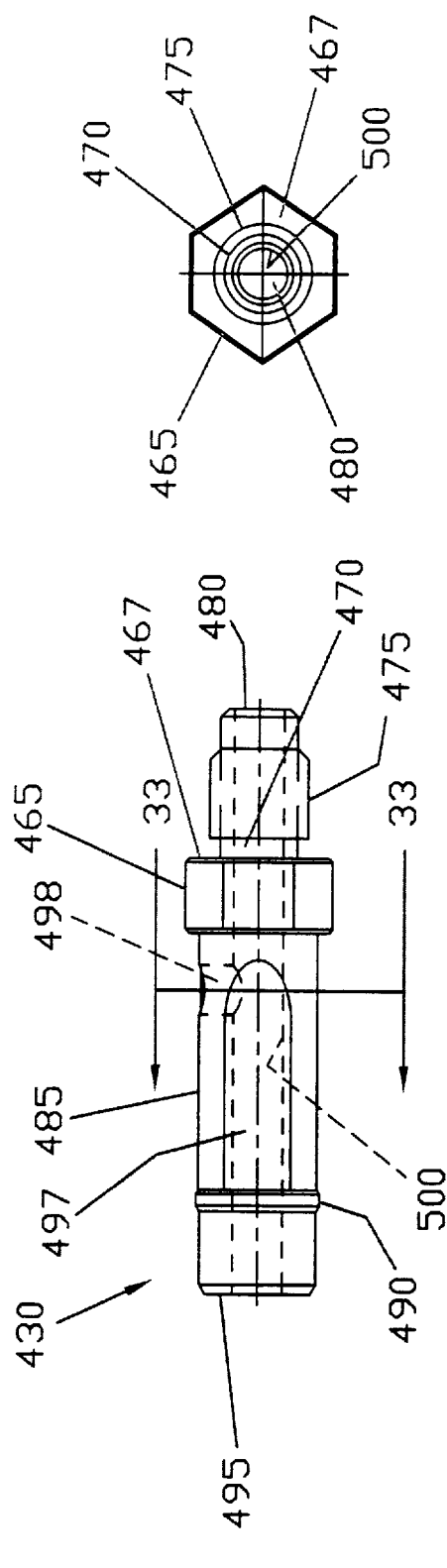
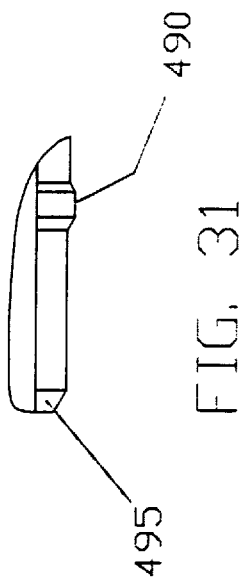
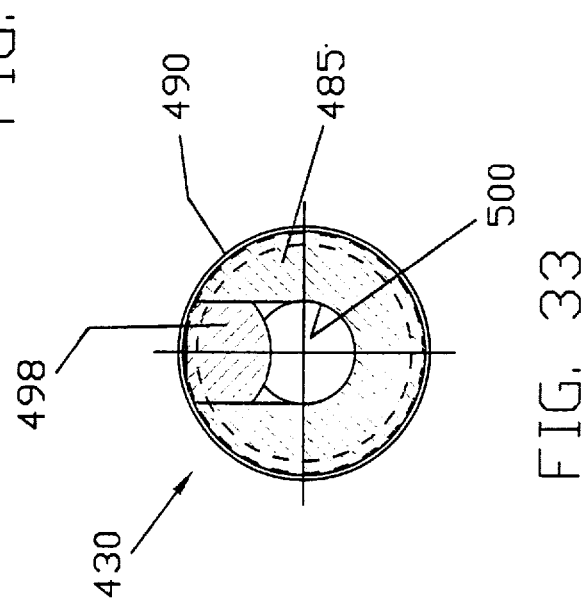

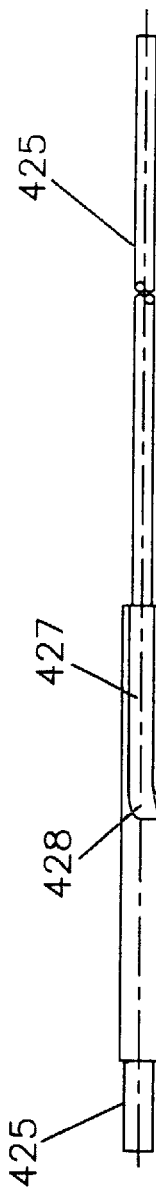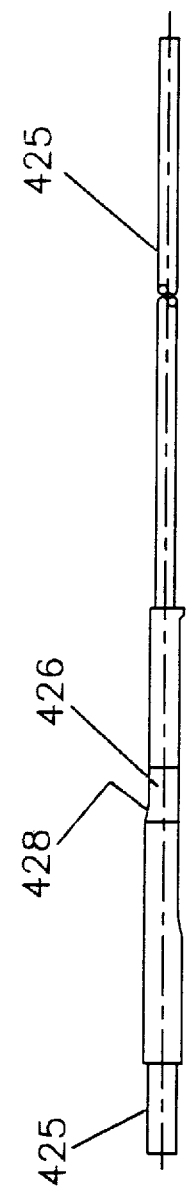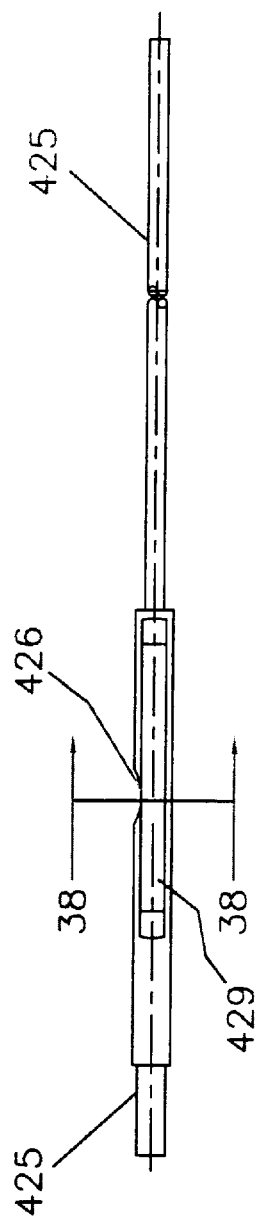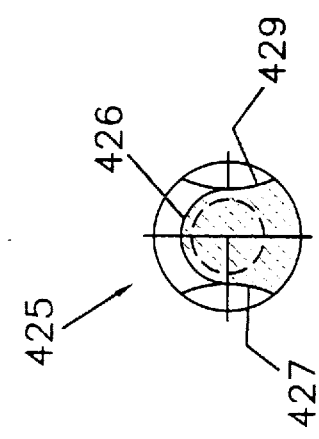
FIG. 34
FIG. 35
FIG. 37
FIG. 38
FIG. 36

SUTURE ANCHOR INSTALLATION TOOL

FIELD OF THE INVENTION

This invention relates to surgical devices in general, and more particularly to devices for attaching suture, bone and/or soft tissue to bone.

BACKGROUND OF THE INVENTION

Bone anchors for attaching suture, bone and/or soft tissue to bone are well known in the art. See, for example, U.S. Pat. Nos. 4,898,156; 5,046,513; 5,192,303; 4,899,743; 4,968,315; 4,946,468; 5,002,550; 5,207,679; and 5,217,486; and U.S. patent applications Ser. Nos. 07/981,011; 08/075,168; 08/030,657; 08/197,927; 08/098,599; and 08/180,425.

Installation tools for deploying such bone anchors in bone are also well known in the art. See, for example, the foregoing U.S. patents and patent applications.

Complete details of the construction and operation of the foregoing exemplary bone anchors and bone anchor installation tools are provided in the above-identified patents and patent applications, which patents and patent applications are hereby incorporated herein by reference.

While the bone anchor installation tools disclosed in the foregoing U.S. patents and patent applications have proven more than satisfactory for most applications, it has been noted that certain problems can occur when using these installation tools in special situations.

More particularly, with some of the foregoing installation tools (e.g. the installation tools disclosed in U.S. Pat. Nos. 4,898,156; 5,046,513; 5,192,303; and 4,899,743), the portion of the tool which carries the anchor (i) is wider than the body of the anchor itself, and (ii) must be positioned within the bone during anchor deployment. As a result of this construction, the bone hole must be formed larger than the body of the anchor in order to permit anchor deployment. This can be a disadvantage in certain situations where it may be necessary to form the smallest possible hole in the bone.

With others of the foregoing installation tools (e.g. the installation tools disclosed in U.S. Pat. No. 5,217,486 and U.S. patent application Ser. No. 08/098,599), the portion of the tool which carries the anchor does not need to be received by the bone during anchor deployment. Instead, only a relatively thin drive pin enters the bone during anchor deployment. The drive pin is formed so that it has a diameter less than the diameter of the anchor body. As a result of this construction, the bone hole can be formed so that it has substantially the same width as the anchor body. However, it has also been found that where the installation tool is being used to set extremely small bone anchors, the drive pin must be so thin that it may bend or otherwise deform in certain circumstances. When this occurs, it may affect anchor deployment and/or render the installation tool unusable for subsequent anchor deployments.

In addition to the foregoing, it has also been found that where the installation tools are being used in conjunction with anchors adapted to attach suture to bone, it can be very helpful to provide suture management means for controlling the disposition of the one or more free suture ends. In this respect it is noted that with some of the foregoing installation tools (e.g. the installation tools disclosed in U.S. Pat. Nos. 4,946,468 and 5,002,550), such suture management means are provided. However, while such suture management means work well enough for most applications, it has been found that alternative suture management means could be helpful in some situations.

OBJECTS OF THE INVENTION

Accordingly, one object of the present invention is to provide an improved bone anchor installation tool.

Another object of the present invention is to provide an improved bone anchor installation tool, wherein the installation tool is adapted to deploy bone anchors of the type adapted to anchor suture to bone.

A further object of the present invention is to provide an improved bone anchor installation tool, wherein the installation tool is adapted to provide improved suture management means for managing the free end or ends of a suture or sutures attached to the bone anchor.

Yet another object of the present invention is to provide an improved bone anchor installation tool, wherein the installation tool is relatively easy to manufacture and relatively inexpensive to produce.

Still another object of the present invention is to provide a novel method for deploying a bone anchor in bone.

SUMMARY OF THE INVENTION

These and other objects of the present invention are achieved through the provision and use of a novel bone anchor installation tool.

In one form of the invention, the installation tool comprises a shaft, a shaft housing adapted to slidingly receive the shaft, the shaft housing having a proximal generally cylindrical portion including an annular rib positioned a predetermined distance from a proximal end thereof, a finger grip, and a stem extending distally from the finger grip, the stem including a threaded portion and terminating in a nose. The tool further comprises a shaft handle fixed to a proximal end of the shaft, the shaft handle comprising a slotted cylindrical portion having an inwardly facing lip disposed proximate a distal end thereof, the slotted cylindrical portion further including a plurality of slots circumferentially positioned in spaced-apart relation, thereby defining a plurality of fingers adapted for gripping the annular rib of the shaft housing, a slotted flange disposed at a proximal end of the slotted cylindrical portion, the slotted flange having a plurality of slots circumferentially disposed in spaced-apart relation, and a headed post extending from a proximal surface of the slotted flange and adapted for retaining a suture free end, the headed post comprising a central column having a hole in which is retained the proximal end of the shaft and a flange disposed at a proximal end of the central column, the central column extending distally from a flat inner surface of the flange. The tool still further comprises an elastomeric grommet disposed around the central column and adapted to releasably hold a length of suture attached to the suture anchor, a sleeve comprising a slotted distal end, the sleeve adapted for slidingly receiving the shaft, and a sleeve handle comprising a proximal portion terminating in a flat proximal end, a distal portion terminating in a rounded distal end, and a bore extending between the proximal end and the distal end, the proximal portion of the sleeve handle further including a threaded counterbore adapted for releasably fastening the threaded portion of the stem, the sleeve handle further including finger grip depressions disposed in opposing circumferential relation thereon and adapted to receive a thumb and finger of a user during installation of the suture anchor. The sleeve housing is provided with an inwardly-directed protrusion therein engageable with notch and slide surfaces of the shaft to determine mobility of the shaft handle axially and rotatively on the shaft housing.

In another form of the invention, a system for deploying a suture anchor in a hole formed in a bone, comprises (i) a suture anchor comprising a generally cylindrical housing, a pair of flexible barbs extending laterally from the housing, and suture attachment means for attaching a length of suture to the housing; and (ii) an installation tool for deploying the suture anchor in bone, the installation tool comprising a body comprising a sleeve, a sleeve handle fixed to the sleeve, and a shaft housing connectable to the sleeve handle, the body having a distal portion and a proximal portion, the distal portion terminating in a distal end surface of the sleeve and the proximal portion terminating in a proximal end surface of the shaft housing, and further wherein an axial passageway extends between the distal end surface and the proximal end surface, with the distal end of the axial passageway being sized to receive at least a portion of the suture anchor therein, and having therein an annular shoulder for seating a proximal end of the suture anchor. The tool further comprises a shaft slidably disposed in the axial passageway, the shaft terminating in a distal end surface and being adapted to move between (i) a first retracted position wherein the shaft's distal end surface is withdrawn sufficiently far into the interior of the axial passageway so as to allow at least a portion of the suture anchor to be received within the distal end of the axial passageway, and (ii) a second extended position wherein the shaft's distal end surface projects out of the distal end of the axial passageway. A peripheral rib is formed on the exterior surface of the shaft housing, and rib engaging means is disposed on a shaft handle connected to the shaft, for yieldably engaging the peripheral rib as the shaft moves from the first retracted position to the second extended position, whereby when the shaft is in the first retracted position, the interaction of the peripheral rib and the rib engaging means prevents the shaft from moving into the second extended position until a sufficient distally-directed force is applied to the shaft to cause the rib engaging means to override the peripheral rib. The tool still further comprises suture management means for managing a free end of a suture attached to the suture anchor when the suture anchor is disposed in the distal end of the axial passageway, the suture management means comprising a recess defining a first surface and an elastomer disposed in the recess so as to yieldably engage the first surface, whereby a free end of a suture may be forced between the first surface and the elastomer and retained there until thereafter forcibly withdrawn. The sleeve housing is provided with an inwardly-directed protrusion therein engageable with notch and slide surfaces of the shaft to determine mobility of the shaft handle axially and rotatively on the shaft housing.

In still another form of the invention, a method for deploying a bone anchor in bone comprises the steps of:

(1) providing a system for deploying a suture anchor in a hole formed in a bone, the system comprising:
  (i) a suture anchor comprising a generally cylindrical housing, a pair of flexible barbs extending laterally from the housing, and suture attachment means for attaching a length of suture to the housing; and
  (ii) an installation tool for deploying the suture anchor in the bone, the installation tool comprising:
    a body comprising a sleeve, a sleeve handle fixed to the sleeve, and a shaft housing connectable to the sleeve handle, the body having a distal portion and a proximal portion, the distal portion terminating in a distal end surface of the sleeve and the proximal portion terminating in a proximal end surface of the shaft housing, and further wherein an axial passageway extends between the distal end surface and the proximal end surface, with the distal end of the axial passageway being sized to receive at least a portion of the suture anchor therein, and having therein an annular shoulder for seating a proximal end of the suture anchor;
    a shaft slidably disposed in the axial passageway, the shaft terminating in a distal end surface and being adapted to move between (i) a first retracted position wherein the shaft's distal end surface is withdrawn sufficiently far into the interior of the axial passageway so as to allow at least a portion of the suture anchor to be received within the distal end of the axial passageway, and (ii) a second extended position wherein the shaft's distal end surface projects out of the distal end of the axial passageway;
    a peripheral rib formed on the exterior surface of the shaft housing;
    rib engaging means disposed on a shaft handle connected to the shaft for yieldably engaging the peripheral rib as the shaft moves from the first retracted position to the second extended position, whereby when the shaft is in the first retracted position, the interaction of the peripheral rib and the rib engaging means prevents the shaft from moving into the second extended position until a sufficient distally-directed force is applied to the shaft to cause the rib engaging means to override the peripheral rib; and
    suture management means for managing a free end of a suture attached to the suture anchor when the suture anchor is disposed in the distal end of the axial passageway, the suture management means comprising a recess defining a first surface and an elastomer disposed in the recess so as to yieldably engage the first surface, whereby a free end of a suture may be forced between the first surface and the elastomer and retained there until thereafter forcibly withdrawn;
    said sleeve housing having an inwardly-directed protrusion therein engageable with notch and slide surfaces of the shaft to determine mobility of the shaft handle axially and rotatively on the shaft housing;

(2) positioning the shaft in the first retracted position;
(3) positioning the suture anchor at least partially within the distal end of the axial passageway and on the sleeve annular shoulder, and positioning a free end of a suture attached to the suture anchor between the first surface and the elastomer;
(4) positioning the distal end of the installation tool against a top surface of the bone having the hole formed therein, with the suture anchor being aligned with the hole;
(5) moving the shaft from the first retracted position to the second extended position to deploy the suture anchor in the bone; and
(6) removing the free end of the suture attached to the suture anchor from between the first surface and the elastomer.

BRIEF DESCRIPTION OF THE DRAWINGS

These and other objects, features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1 is a side elevational view of a fully assembled installation tool, wherein the installation tool's shaft is in its first retracted position;

FIG. 2 is a side elevational view of the same fully assembled installation tool, wherein the installation tool's shaft is in its second extended position;

FIG. 4 is a side elevational view of a sleeve which constitutes part of the installation tool;

FIG. 5 is an end view showing the distal end of the sleeve;

FIG. 6 is a side elevational view of a sleeve handle which constitutes part of the installation tool;

FIG. 7 is an end view showing the proximal end of the sleeve handle;

FIG. 8 is a side elevational view of a shaft which constitutes part of the installation tool's shaft subassembly;

FIG. 9 is an end view showing the proximal end of the shaft;

FIG. 10 is a side elevational view of a shaft housing which constitutes part of the installation tool's shaft subassembly;

FIG. 11 is a cross-sectional view taken along line 11—11 of FIG. 10;

FIG. 12 is an end view showing the proximal end of the shaft housing;

FIG. 13 is a side view in section of a shaft handle which constitutes part of the installation tool's shaft subassembly;

FIG. 14 is an end view showing the proximal end of the shaft handle;

FIG. 15 is a side view partially in section showing a bone anchor installed in the distal end of the bone anchor installation tool of the present invention;

FIG. 16 is a side view partially in section showing the bone anchor and bone anchor installation tool of FIG. 15, wherein the distal end of the installation tool is in engagement with the outer surface of a bone and the bone anchor is about to be deployed in that bone;

FIG. 17 is a view like that of FIG. 16, except that the bone anchor has been deployed in the bone;

FIG. 21 is an interrupted side elevational view of a sleeve handle portion of the tool of FIG. 18 and the sleeve portion fixed thereto;

FIG. 22 is an end elevational view of the handle and sleeve portions of FIG. 21;

FIG. 23 is a side elevational view of the sleeve handle of FIG. 18;

FIG. 24 is an end elevational view of the sleeve handle of FIG. 23;

FIG. 25 is a sectional view taken along line 25—25 of FIG. 24;

FIG. 26 is an interrupted side elevational view, in part broken away and in part in section, of the installation tool of FIG. 18;

FIG. 27 is a centerline sectional view of a shaft handle portion of the tool of FIG. 18;

FIG. 28 is an end view of the shaft handle portion of FIG. 27;

FIG. 29 is an enlarged view of a portion of the shaft handle of FIG. 27;

FIG. 30 is a side elevational view of a shaft housing portion of the tool of FIG. 18;

FIG. 31 is an enlarged elevational view of a portion of the shaft housing of FIG. 30;

FIG. 32 is an end elevational view of the shaft housing of FIG. 30;

FIG. 33 is a sectional view taken along line 33—33 of FIG. 30;

FIG. 34 is a side elevational view of a shaft portion of the tool of FIG. 18;

FIG. 35 is a top plan view of the shaft of FIG. 34;

FIG. 36 is an end view of the shaft of FIG. 35;

FIG. 37 is a side elevational view of the shaft of FIG. 35; and

FIG. 38 is a sectional view taken along line 38—38 of FIG. 37.

DETAILED DESCRIPTION OF THE PREFERRED EMBODIMENT

Looking first at FIGS. 1 and 2, a bone anchor installation tool 5 is shown which comprises a preferred embodiment of the present invention. Installation tool 5 generally comprises a shaft subassembly 10 (FIGS. 1–3), a sleeve 15 (FIGS. 1, 2, 4 and 5) and a sleeve handle 20 (FIGS. 1, 2, 6 and 7).

Figure 3:
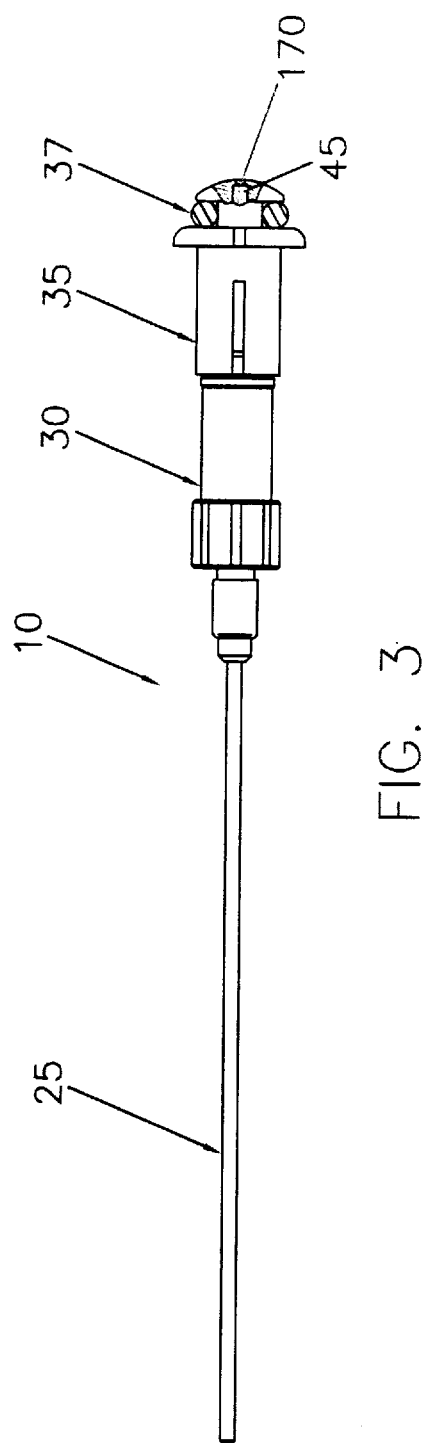
FIG. 3 is a side elevational view, in partial section, of the installation tool's shaft subassembly.

More particularly, and looking now at FIG. 3, shaft subassembly 10 generally comprises a shaft 25, a shaft housing 30, a shaft handle 35 and a rubber grommet 37.

Shaft 25 is shown in greater detail in FIGS. 8 and 9. Shaft 25 comprises a first cylindrical portion 40 and a second cylindrical portion 45. Second cylindrical portion 45 has a smaller diameter than first cylindrical portion 40. First cylindrical portion 40 and second cylindrical portion 45 together define an annular shoulder 50. First cylindrical portion 40 terminates in a distal end surface 55. Second cylindrical portion 45 terminates in a proximal end surface 60.

Shaft housing 30 is shown in greater detail in FIGS. 10–12. Shaft housing 30 comprises a fluted finger grip 65 having a flat distal surface 67. A stem 70 extends distally away from the fluted finger grip's flat distal surface 67. Stem 70 includes a threaded portion 75 and terminates in a chamfered distal nose 80. Shaft housing 30 also comprises a cylindrical portion 85 extending proximally away from fluted finger grip 65. Cylindrical portion 85 includes an annular rib 90 and terminates in a flat proximal end surface 95. A central passageway 100 extends through shaft housing 30, from chamfered distal nose 80 of stem 70 to flat proximal end surface 95 of cylindrical portion 85.

Shaft handle 35 is shown in greater detail in FIGS. 13 and 14. Shaft handle 35 comprises a slotted cylindrical portion 105, a slotted flange 110 and a T-shaped post 115. More particularly, slotted cylindrical portion 105 comprises an inwardly facing lip 125 and four slots 130. Slots 130 are disposed in equally-circumferentially-spaced relation about the circumference of slotted cylindrical portion 105. In essence, slots 130 divide slotted cylindrical portion 105 into four longitudinally-extending fingers. Slotted flange 110 comprises four slots 135. Slots 135 are disposed in equally-circumferentially-spaced relation about the circumference of slotted flange 110. Slots 135 of slotted flange 110 are aligned with slots 130 of slotted cylindrical portion 105. Slotted flange 110 terminates in a flat distal surface 137 and in a proximal surface 140. The flange's proximal surface 140 is preferably rounded somewhat at its circumferential edge 142, adjacent to where proximal surface 140 meets flat distal surface 137. T-shaped post 115 comprises a cylindrical central column 145 and an annular flange 150. Flange 150 terminates in a rounded proximal surface 155 and in a flat distal surface 160. A rounded circumferential edge 165 is defined by the intersection of rounded proximal surface 155 and flat distal surface 160. A hole 170 extends axially through slotted flange 110 and into T-shaped post 115, and communicates with the interior of slotted cylindrical portion 105. Hole 170 is coaxial with, and communicates with, another hole 171 which opens on rounded proximal surface 155.

Rubber grommet 37 (FIGS. 1–3) comprises a toroidal shaped piece of elastomer adapted to be positioned on shaft handle 35. More particularly, rubber grommet 37 is adapted to be fit over the shaft handle's cylindrical central column 145 so as to be compressed between flat proximal surface 140 of slotted flange 110 and flat distal surface 160 of annular flange 150.

Shaft subassembly 10 is assembled as follows. First, the shaft's second portion 45 is passed through the shaft housing's central passageway 100 until the shaft housing's chamfered distal nose 80 engages the shaft's annular shoulder 50. Then shaft handle 35 is passed over the proximal end of shaft housing 30 until the proximal end of shaft 25 enters the shaft handle's hole 170. The proximal end of shaft 25 is then made fast in hole 170 by welding, using access hole 171. On account of the foregoing construction, shaft 25 and shaft handle 35 thereafter operate as a single unit, with shaft housing 30 being slidably captured on shaft 25 between the shaft's annular shoulder 50 and the shaft handle's distal surface 137, as will hereinafter be described in further detail. Once this has been accomplished, rubber grommet 37 is then mounted onto the shaft handle's cylindrical central column 145.

Looking next at FIGS. 4 and 5, sleeve 15 comprises a distal portion 175 and a proximal portion 180. Distal portion 175 comprises four slots 185. Slots 185 are equally-circumferentially-spaced about the circumference of sleeve 15. Slots 185 open on the sleeve's distal end surface 190. The proximal portion of sleeve 15 is flared outwardly at 195 and terminates in a proximal end surface 200. A central passageway 203 extends between distal end surface 190 and proximal end surface 200.

Looking next at FIGS. 6 and 7, sleeve handle 20 comprises a distal portion 205 and a proximal portion 210. Distal portion 205 terminates in a rounded distal end surface 215 and proximal portion 210 terminates in a flat proximal end surface 220. Sleeve handle 20 also includes a bore 225 and a counterbore 230. Bore 225 opens on the sleeve handle's rounded distal end surface 215 and counterbore 230 opens on the sleeve handle's flat proximal end surface 220. Bore 225 and counterbore 230 meet at an internal angled shoulder 235. The proximal portion of counterbore 230 is threaded at 240. A plurality of finger grip depressions 245 are formed in the outer surface of sleeve handle 20.

The complete bone anchor installation tool 5 is assembled as follows. First, sleeve 15 is passed distal end first through counterbore 230 and bore 225 of sleeve handle 20, until the sleeve's flared portion 195 engages the sleeve handle's internal angled shoulder 235. Then the assembled shaft subassembly 10 is passed distal end first through counterbore 230 of sleeve handle 20 and central passageway 203 of sleeve 15, until chamfered distal nose 80 of shaft subassembly 10 enters counterbore 230 of sleeve handle 20. Shaft subassembly 10 is then rotated so that the shaft housing's threaded portion 75 engages threads 240 of sleeve handle 20. Shaft subassembly 10 is turned until the shaft housing's flat distal surface 67 engages the sleeve handle's proximal end surface 220. At this point, chamfered distal nose 80 of shaft subassembly 10 will make a close fit with proximal end surface 200 of sleeve 15, so as to maintain the longitudinal position of sleeve 15 relative to the remainder of the installation tool. At the same time, however, sleeve 15 is free to rotate relative to the remainder of the installation tool.

When bone anchor installation tool 5 is assembled in the foregoing manner, its shaft 25 will be free to move between (i) a first retracted position (FIG. 1) wherein the shaft's annular shoulder 50 is substantially in engagement with the shaft housing's chamfered distal nose 80, and the shaft handle's inwardly facing lip 125 is on the proximal side of, and substantially in engagement with, the shaft housing's annular rib 90, and the shaft's distal end surface 55 is withdrawn into the interior of sleeve 15; and (ii) a second extended position (FIG. 2) wherein the shaft handle's flat distal end surface 137 is in engagement with the shaft housing's flat proximal end surface 95, and the shaft handle's inwardly facing lip 125 is on the distal side of, and substantially displaced from, the shaft housing's annular rib 90, and the shaft's distal end surface 55 protrudes a substantial distance beyond the sleeve's distal end surface 190.

Bone anchor installation tool 5 is preferably used to deploy a suture anchor of the sort disclosed in the aforementioned U.S. Pat. No. 5,217,486 and/or a suture anchor of the sort disclosed in the aforementioned U.S. patent application Ser. No. 08/197,927, i.e., bone anchor installation tool 5 is preferably used to deploy a suture anchor of the sort comprising (i) a generally cylindrical body, (ii) a pair of flexible barbs extending laterally out of the side of the body, and (iii) suture attachment means for attaching a length of suture to the body. Of course, bone anchor installation tool 5 may also be used to deploy other types of bone anchors in bone or other types of fasteners in a workpiece, so long as such bone anchor or fastener is compatible with the present invention.

Bone anchor installation tool 5 is intended to be used as follows. First, installation tool 5 is positioned so that its shaft 25 is in its aforementioned first retracted position, wherein the shaft's annular shoulder 50 is substantially in engagement with the shaft housing's chamfered distal nose 80, and the shaft handle's inwardly facing lip 125 is on the proximal side of, and substantially in engagement with, the shaft housing's annular rib 90, and the shaft's distal end surface 55 is withdrawn into the interior of sleeve 15 (FIG. 1). It is to be appreciated that bone anchor installation tool 5 will be inclined to remain in its aforementioned first retracted position until it is thereafter forced to assume another position, inasmuch as the shaft housing's annular rib 90 will tend to inhibit passage of the shaft handle's inwardly facing lip 125.

Next, and looking now at FIG. 15, a suture anchor 300 is loaded into the distal end of sleeve 15 so that the suture anchor's proximal end 305 rests against the shaft's distal end surface 55, with the suture anchor's two barbs 310 extending out through two of the sleeve's slots 185 and the suture anchor's two lengths of suture 315 extending out through the other two of the sleeve's slots 185.

The two lengths of suture 315 are then extended tautly back along the length of the installation tool and threaded through one or more of the shaft handle's slots 135 before being wound tightly around the shaft handle's cylindrical central column 145, in the space between rubber grommet 37 and the shaft handle's surface 140. The resilient engagement of rubber grommet 37 with the shaft's surface 140 thereafter serves to keep the two lengths of suture 315 securely in place at the proximal end of the installation tool, yet allow a surgeon to easily pull the two lengths of suture free from the installation tool when needed. Furthermore, by ensuring that the two lengths of suture 315 extend tautly back along the length of installation tool 5 prior to being secured in place via rubber grommet 37, the two lengths of suture 315 will serve to ensure that suture anchor 300 cannot become prematurely disengaged from the distal end of the installation tool.

Next, and looking now at FIG. 16, the installation tool is manipulated so as to position the distal portion of suture anchor 300 within the top of a hole 320 formed in a bone 325, with the distal end of sleeve 15 engaging the top surface 330 of the bone.

Suture anchor 300 can then be deployed in bone 325 by pressing on the shaft handle's proximal surface 155 so as to urge the installation tool's shaft 25 into its aforementioned second extended position. As this occurs, the shaft handle's inwardly facing lip 125 will be forced over the shaft housing's annular rib 90 as the shaft handle's flat distal end surface 137 moves into engagement with the shaft housing's flat proximal end surface 95 and the shaft's distal end surface 55 moves out of the sleeve's distal end. As a consequence of this action, suture anchor 300 will be driven out of the distal end of sleeve 15 and into bone 325, with the suture anchor's barbs 310 securing the anchor in place and with the two lengths of suture 315 extending back out of the bone hole to the installation tool. The two lengths of suture 315 may then be unwound from the installation tool before the installation tool is removed from the surgical site.

Figure 18:
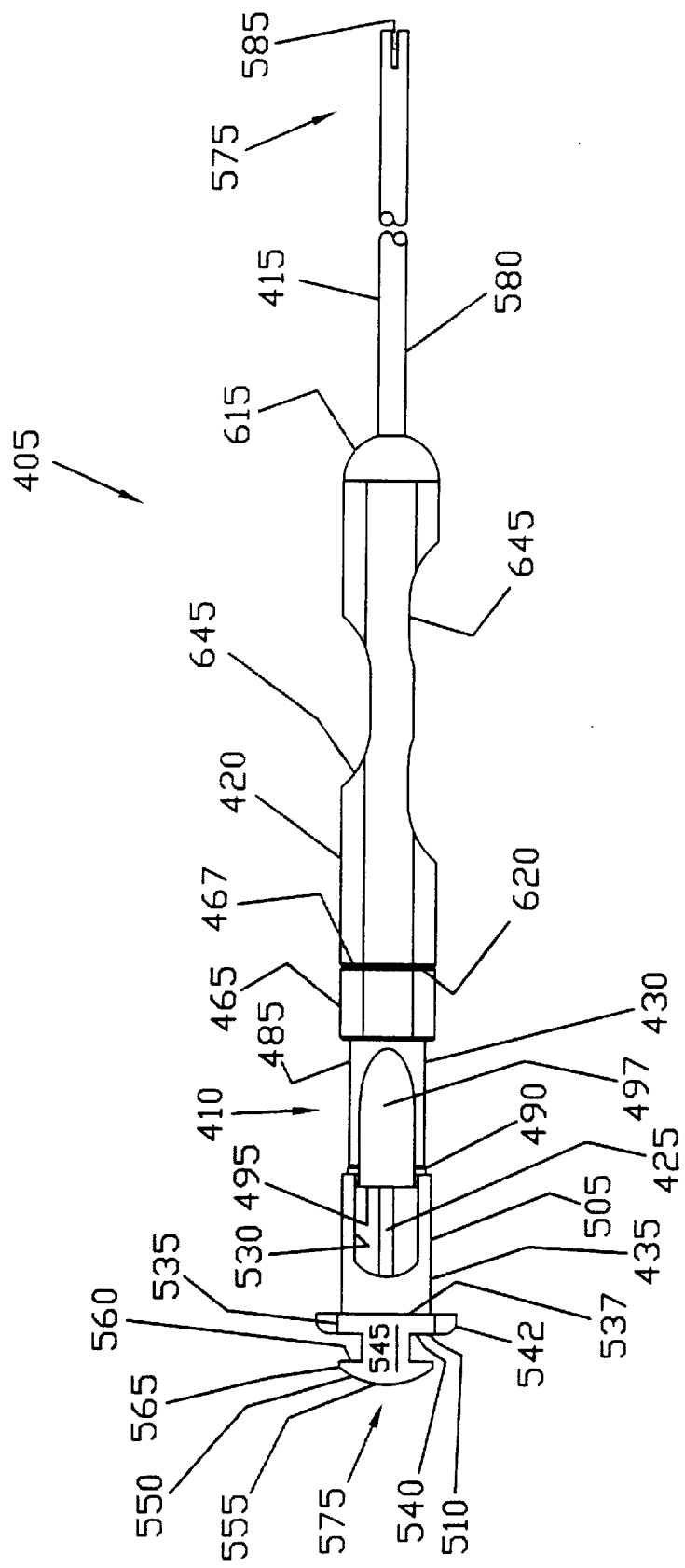
FIG. 18 is a side elevational view of an alternative embodiment of installation tool, wherein the installation tool shaft is in a retracted position.
Figure 19:
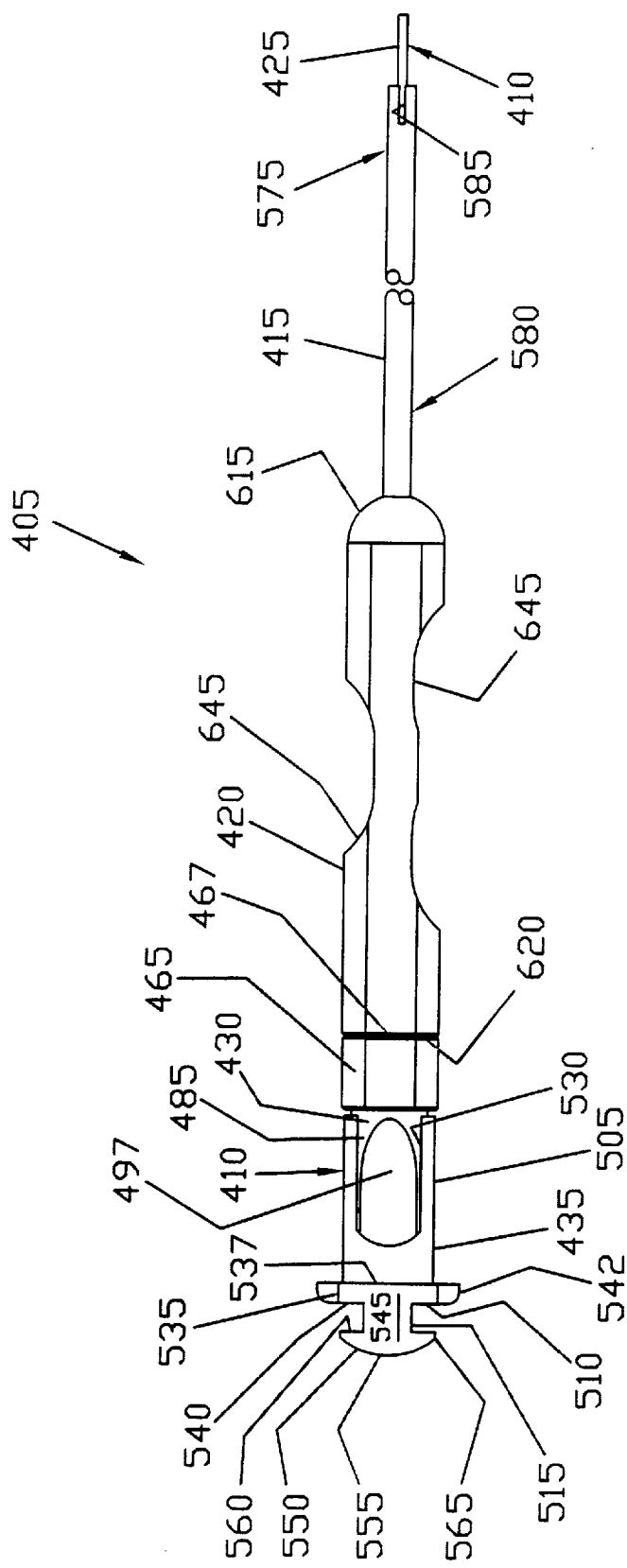
FIG. 19 is similar to FIG. 18, but showing the installation tool shaft in an extended position.
Figure 20:
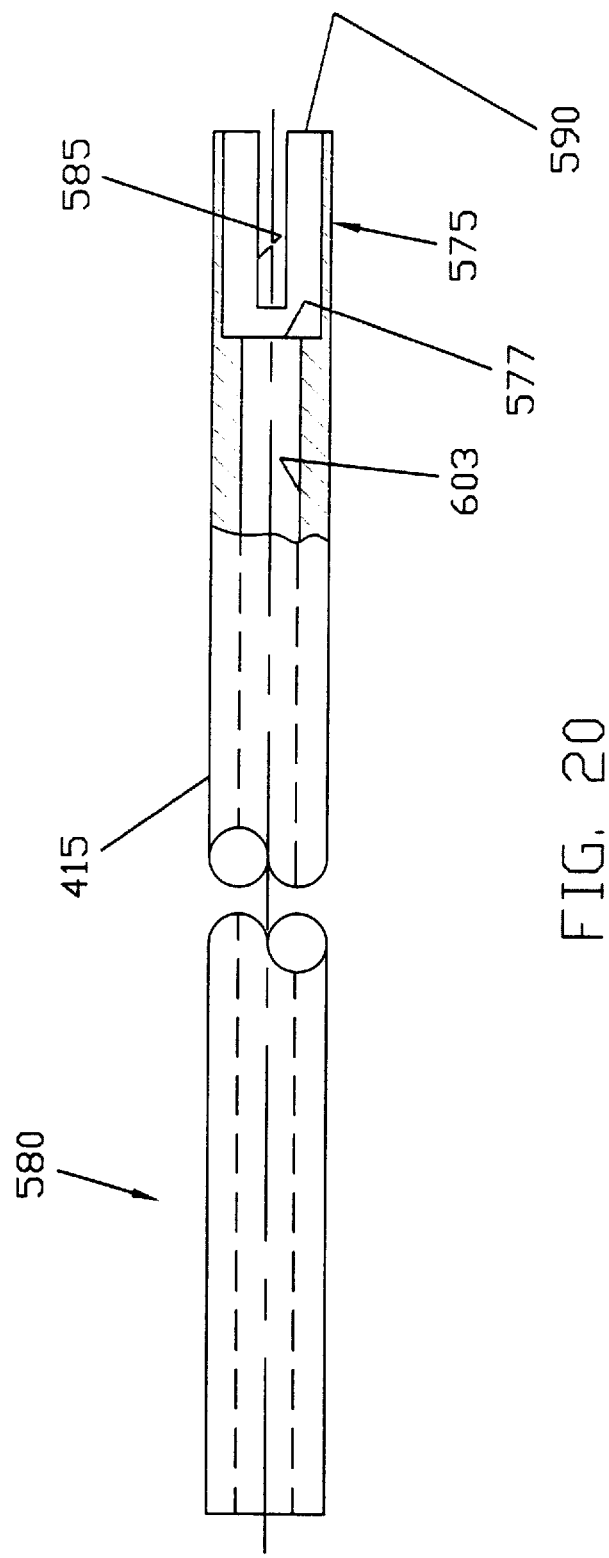
FIG. 20 is an interrupted side elevational view, in part broken away, and in part in section, of a sleeve portion of the tool of FIG. 18.

Looking at FIGS. 18 and 19, an alternative embodiment of bone anchor installation tool 405 is shown which comprises a shaft subassembly 410, and a sleeve 415 fixed to, or integral with, a sleeve handle 420.

More particularly, and looking now at FIG. 26, shaft subassembly 410 generally comprises a shaft 425, a shaft housing 430, a shaft handle 435 and a rubber grommet 437.

Shaft housing 430 is shown in greater detail in FIGS. 30–33. Shaft housing 430 comprises a hexagonal nut finger grip 465 having a flat distal surface 467. A stem 470 extends distally away from the finger grip's flat distal surface 467. Stem 470 includes a threaded portion 475 and terminates in a chamfered distal nose 480. Shaft housing 430 also comprises a cylindrical portion 485 extending proximally away from finger grip 465. Cylindrical portion 485 includes an annular rib 490 and terminates in a flat proximal end surface 495. Cylindrical portion 485 further includes elongated axially-extending recesses 497 which are aligned with slots 530 (FIGS. 18 and 19). A central passageway 500 (FIGS. 30, 32, 33) extends through shaft housing 430, from chamfered distal nose 480 of stem 470 to flat proximal end surface 495 of cylindrical portion 485.

Shaft handle 435 is shown in greater detail in FIGS. 26–29. Shaft handle 435 comprises a slotted cylindrical portion 505, a slotted flange 510 and a headed post 515. More particularly, slotted cylindrical portion 505 comprises an inwardly facing lip 525 and two relatively wide slots 530. Slots 530 are disposed in opposed relation about the circumference of slotted cylindrical portion 505. In essence, slots 530 divide slotted cylindrical portion 505 into two longitudinally-extending fingers. The wide slots 530, preferably occupying at least 40% of the circumference of the cylindrical portion 505, facilitate easier cleaning of the tool 405 than is the case with cylindrical portion 105 of tool 5. Slotted flange 510 comprises a plurality of slots 535 disposed in equally circumferentially spaced relation about the circumference of slotted flange 510. Slotted flange 510 terminates in a flat distal surface 537 and in a proximal surface 540. The flange's proximal surface 540 is preferably rounded somewhat at its circumferential edge 542, adjacent to where proximal surface 540 meets flat distal surface 537. Headed post 515 comprises a cylindrical central column 545 and an annular flange 550. Flange 550 terminates in a rounded proximal surface 555 and in a flat distal surface 560. A rounded circumferential edge 565 is defined by the intersection of rounded proximal surface 555 and flat distal surface 560. A hole 570 (FIG. 27) extends axially through slotted flange 510 and into headed post 515, and communicates with the interior of slotted cylindrical portion 505. Hole 570 is coaxial with, and communicates with, another hole 571 which opens on rounded proximal surface 555.

Rubber grommet 437 (FIGS. 26 and 27) comprises a toroidal shaped piece of elastomer adapted to be positioned on shaft handle 435. More particularly, rubber grommet 437 is adapted to be fit over the shaft handle's cylindrical central column 545 so as to be compressed between flat proximal surface 540 of slotted flange 510 and flat distal surface 560 of annular flange 550.

In assembly of the shaft subassembly 410, the shaft 425 is passed through the shaft housing's central passageway 500. Then shaft handle 435, with shaft 425 fixed thereto, is passed over the proximal end of shaft housing 430 with the shaft handle slots 530 aligned, respectively, with the shaft housing elongated recesses 497, and the shaft 425 extending through shaft housing 430. The shaft 425 and shaft handle 435, fixed together, operate as a single unit, with shaft housing 430 being slidably disposed on shaft 425. Elastomer grommet 437 is then mounted onto the shaft handle's cylindrical central column 545.

Looking next at FIGS. 20–25, sleeve 415 comprises a distal portion 575 and a proximal portion 580. Distal portion 575 comprises at least two slots 585. Slots 585 are equally circumferentially spaced about the circumference of sleeve 415. Slots 585 open on the sleeve's distal end surface 590. The sleeve distal portion 575 is further provided with an internal annular shoulder 577 (FIG. 20), for receiving the proximal end 305 of suture anchor 300. The proximal portion 580 of sleeve 415 is joined to, or integral with, sleeve handle 420. A central passageway 603 extends between distal and proximal ends of sleeve 415.

Looking next at FIGS. 23–25, sleeve handle 420 comprises a distal portion 605 and a proximal portion 610. Distal portion 605 terminates in a rounded distal end surface 615 and proximal portion 610 terminates in a flat proximal end surface 620. Sleeve handle 420 also includes a bore 625 and a counterbore 630. Bore 625 opens on the sleeve handle's rounded distal end surface 615 and counterbore 630 opens on the sleeve handle's flat proximal end surface 620. Bore 625 and counterbore 630 meet at an internal angled shoulder 635. The proximal portion of counterbore 630 is threaded at 640. A plurality of finger grip depressions 645 are formed in the outer surface of sleeve handle 420.

The complete bone anchor installation tool 405 is assembled as follows. The assembled shaft subassembly 410 is passed distal end first through counterbore 630 of sleeve handle 420 and central passageway 603 of sleeve 415, until chamfered distal nose 480 of shaft subassembly 410 enters counterbore 630 of sleeve handle 420. Shaft subassembly 410 is then rotated so that the shaft housing's threaded portion 475 engages threads 640 of sleeve handle 420. Shaft subassembly 410 is turned until the shaft housing's flat distal surface 467 engages the sleeve handle's proximal end surface 620.

When bone anchor installation tool 405 assembled in the foregoing manner, its shaft 425 will be free to move between (i) a first retracted position (FIG. 18) wherein the shaft housing's inwardly facing lip 525 is on the proximal side of, and substantially in engagement with, the shaft housing's annular rib 490, and the shaft's distal end is withdrawn into the interior of sleeve 415; and (ii) a second extended position (FIG. 19) wherein the shaft handle's inwardly facing lip 525 is on the distal side of, and substantially displaced from, the shaft housing's annular rib 490, and the shaft's distal end protrudes a substantial distance beyond the sleeve's distal end surface 590.

Bone anchor installation tool 405 preferably is used to deploy a suture anchor of the sort disclosed in the aforementioned U.S. Pat. No. 5,217,486 and/or a suture anchor of the sort disclosed in the aforementioned U.S. patent application Ser. No. 08/197,927, i.e., bone anchor installation tool 405 preferably is used to deploy a suture anchor of the sort comprising (i) a generally cylindrical body, (ii) a pair of flexible barbs extending laterally out of the side of the body, and (iii) suture attachment means for attaching a length of suture to the body. Of course, bone anchor installation tool 405 may also be used to deploy other types of bone anchors in bone or other types of fasteners in a workpiece, so long as such bone anchor or fastener is compatible with the present invention.

Bone anchor installation tool 405 is intended to be used as follows. First, installation tool 405 is positioned so that its shaft 425 is in its aforementioned first retracted position, wherein the shaft handle's inwardly facing lip 525 is on the proximal side of, and substantially in engagement with, the shaft housing's annular rib 490, and the shaft's distal end is withdrawn into the interior of sleeve 415 (FIG. 18). It is to be appreciated that bone anchor installation tool 405 will be inclined to remain in its aforementioned first retracted position until it is thereafter forced to assume another position, inasmuch as the shaft housing's annular rib 490 will tend to inhibit passage of the shaft handle's inwardly facing lip 525.

Next, suture anchor 300 is loaded into the distal end of sleeve 415 so that the suture anchor's proximal end rests against the sleeve shoulder 577, with the suture anchor's two barbs 310 and two lengths of suture 315 extending out through the sleeve's slots 585.

The two lengths of suture 315 are then extended tautly back along the length of the installation tool and threaded through one or more of the shaft handle's slots 535 before being wound tightly around the shaft handle's cylindrical central column 545, in the space between rubber grommet 437 and the shaft handle's surface 540. The resilient engagement of rubber grommet 437 with the shaft's surface 540 thereafter serves to keep the two lengths of suture 315 securely in place at the proximal end of the installation tool, yet allow a surgeon to easily pull the two lengths of suture free from the installation tool when needed. Furthermore, by ensuring that the two lengths of suture 315 extend tautly back along the length of installation tool 405 prior to being secured in place via rubber grommet 437, the two lengths of suture 315 will serve to ensure that suture anchor 300 cannot become prematurely disengaged from the distal end of the installation tool.

Next, the installation tool 405 is manipulated so as to position the distal portion of suture anchor 300 within the top of the hole 320 formed in the bone 325, with the distal end of sleeve 415 engaging the top surface 330 of the bone, as depicted in FIG. 16 with respect to installation tool 5.

Suture anchor 300 can then be deployed in bone 325 by pressing on the shaft handle's proximal surface 555 so as to urge the installation tool's shaft 425 into its aforementioned second extended position. As this occurs, the shaft handle's inwardly facing lip 525 is forced over the shaft housing's annular rib 490 as the shaft handle's flat distal end surface 537 moves into engagement with the shaft housing's flat proximal end surface 495 and the shaft's distal end moves out of the sleeve's distal end. As a consequence of this action, suture anchor 300 is driven out of the distal end of sleeve 415 and into bone 325, with the suture anchor's barbs 310 securing the anchor in place and with the two lengths of suture 315 extending back out of the bone hole to the installation tool. The two lengths of suture 315 may then be unwound from the installation tool before the installation tool is removed from the surgical site.

Referring to FIGS. 30 and 33, it will be seen that shaft housing 430 is provided with a cross-pin 498, or similar inwardly-directed protrusion, which extends slightly into central passageway 500. Referring to FIGS. 34–38, it will be seen that shaft 425 is provided with a notch 426 which receives the protrusion 498.

The shaft handle 435 is mounted on the shaft housing 430 such that the shaft handle slots 530 are in alignment with the shaft housing elongated recesses 497. The protrusion 498 is received by a slide surface 427 on shaft 425. When shaft handle 435 is pushed distally, to cause shaft handle lip 525 to override rib 490, protrusion 498 engages a shoulder 428 to stop axial movement of shaft 425, with the distal end of shaft 425 still within sleeve 415. The shaft handle 435 is then rotated 180° to bring slide wall 429 into alignment with protrusion 498, allowing shaft 425 to move distally so as to extend the distal end of shaft 425 out of the distal end 590 of sleeve 415. At this point shaft handle 435 is prevented from rotating on shaft housing 430. Thus, when suture 315 is wound between grommet 437 and surface 540, shaft handle 435 will not rotate, but remains stationery to facilitate the winding of suture 315 thereon.

To disassemble the tool 405, shaft handle 435 is urged in a clockwise turning direction while being moved distally along shaft housing 430. At a point, notch 426 receives protrusion 498 and permits turning of shaft handle 435 on shaft housing 430 180°, and withdrawal of shaft handle 435 and shaft 425 from shaft housing 430. Shaft housing 430 may then be unscrewed from sleeve handle 420.

Thus, the shaft housing protrusion 498 cooperates with the notch and slide surfaces 426, 427, and 429 of the shaft 425 to determine axial and rotative mobility of the shaft handle 435 on the shaft housing 430. Such cooperation prevents unwanted movement but permits beneficial movement.

The above described alternative embodiment provides advantages over the above first-described embodiment. Inasmuch as the shaft handle 435 does not rotate on shaft housing 430 during a bone anchor emplacement, suture 315 may be more easily wound between grommet 437 and surface 540. Further, the alternative embodiment is easier to clean because of (1) the wide slots 530 in the shaft handle 435 and (2) the separability of the tool into three sections:

(1) the shaft handle 435 and shaft 425, (2) the shaft housing 430, and (3) the sleeve handle 420 and sleeve 415.

Advantages Of The Present Invention

Numerous advantages are obtained by using either embodiment of the present invention.

For one thing, an improved bone anchor installation tool is provided.

For another thing, an improved bone anchor installation tool is provided, wherein the installation tool is adapted to deploy bone anchors of the type adapted to anchor suture to bone.

Also, an improved bone anchor installation tool is provided, wherein the installation tool is adapted to provide improved suture management means for managing the free end or ends of a suture or sutures attached to the bone anchor.

Furthermore, an improved bone anchor installation tool is provided, wherein the installation tool is relatively easy to manufacture and relatively inexpensive to produce.

In addition, an improved method is provided for deploying a bone anchor in bone.

Still other advantages of the invention will be obvious to those skilled in the art.

Modifications Of The Preferred Embodiment

It will, of course, be appreciated that certain modifications may be made to the foregoing preferred embodiment of the present invention without departing from the scope of the present invention.

Thus, for example, the number of slots provided in the distal end of sleeve 415, may be varied.

Furthermore, the number of slots provided in slotted cylindrical portion 105, 505 and/or the number of slots provided in slotted flange 110, 510, may be varied.

Also, finger grip 65 can be formed with an exterior surface which is knurled rather than fluted or hexagonal, or finger grip 65 can be formed with a relatively smooth surface, if desired.

Additionally, suture 315 can be held to the proximal end of the installation tool by wrapping it around cylindrical central column 145, 545 between rubber grommet 37, 437 and the shaft handle's flat surface 160, 560 rather than between rubber grommet 37, 437 and the shaft handle's surface 140, 540.

These and other changes will be obvious to a person skilled in the art, and are considered to be within the scope of the present invention.

What is claimed is:

1. An installation tool for deploying a suture anchor, said installation tool comprising:

a shaft;

a shaft housing adapted to slidingly receive said shaft, said shaft housing having a proximal generally cylindrical portion including an annular rib positioned a predetermined distance from a proximal end thereof, a finger grip, and a stem extending distally from said finger grip, said stem including a threaded portion and terminating in a nose;

a shaft handle fixed to a proximal end of said shaft, said shaft handle comprising a slotted cylindrical portion having an inwardly facing lip disposed proximate a distal end thereof, said slotted cylindrical portion further including a plurality of slots circumferentially positioned in spaced-apart relation, thereby defining a plurality of fingers adapted for gripping said annular rib of said shaft housing, a slotted flange disposed at a proximal end of said slotted cylindrical portion, said slotted flange having a plurality of slots each circumferentially disposed in spaced-apart relation, and a headed post extending from a proximal surface of said slotted flange and adapted for retaining a suture free end, said headed post comprising a central column having a hole in which is retained said proximal end of said shaft and a flange disposed at a proximal end of said central column, said central column extending distally from a flat inner surface of said flange;

an elastomeric grommet disposed around said central column and adapted to releasably hold a length of suture attached to said suture anchor;

a sleeve comprising a slotted distal end, said sleeve adapted for slidingly receiving said shaft; and a sleeve handle comprising a proximal portion terminating in a flat proximal end, a distal portion terminating in a rounded distal end, and a bore extending between said proximal end and said distal end, said proximal portion of said sleeve handle further including a threaded counterbore adapted for releasably fastening said threaded portion of said stem, said sleeve handle further including finger grip depressions disposed in opposing circumferential relation thereon and adapted to receive a thumb and finger of a user during installation of said suture anchor;

said shaft housing having an inwardly-directed protrusion therein engageable with notch and slide surfaces of said shaft to determine mobility of said shaft handle axially and rotatively on said shaft housing.

2. An installation tool according to claim 1 wherein said internal inwardly-directed protrusion and said shaft notch and slide surfaces prevent rotation of said shaft handle on said shaft housing during a bone anchor installation.

3. An installation tool according to claim 2 wherein said protrusion and said notch and slide surfaces cooperate with each other to permit rotation of said shaft handle on said shaft housing for separation of said shaft handle and said shaft from said shaft housing upon completion of said bone anchor installation.

4. An installation tool according to claim 1 wherein said shaft housing is provided with a plurality of oppositely disposed elongated axially extending recesses, and wherein each of said recesses is alignable with one of said shaft handle slots to position said protrusion to permit relative axial movement between said shaft handle and said shaft housing.

5. An installation tool according to claim 1 wherein said sleeve is provided with an internal annular shoulder for seating a proximal end of the suture anchor.

6. An installation tool according to claim 1 wherein said shaft handle and shaft are disconnectable from said sleeve, sleeve handle, and shaft housing, and said shaft housing is disconnectable from said sleeve handle and sleeve.

7. A system for deploying a suture anchor in a hole formed in a bone, said system comprising:

(i) a suture anchor comprising a generally cylindrical housing, a pair of flexible barbs extending laterally from said housing, and suture attachment means for attaching a length of suture to said housing; and (ii) an installation tool for deploying said suture anchor in the bone, said installation tool comprising:

a body comprising a sleeve, a sleeve handle fixed to said sleeve, and a shaft housing connectable to said sleeve handle, said body having a distal portion and a proximal portion, said distal portion terminating in a distal end surface of said sleeve and said proximal portion terminating in a proximal end surface of said shaft housing, and further wherein an axial passageway extends between said distal end surface and said proximal end surface, with said distal end of said axial passageway being sized to receive at least a portion of said suture anchor therein, and having therein an annular shoulder for seating a proximal end of said suture anchor;

a shaft slidably disposed in said axial passageway, said shaft terminating in a distal end surface and being adapted to move between (i) a first retracted position wherein said shaft's distal end surface is withdrawn sufficiently far into the interior of said axial passageway so as to allow at least a portion of said suture anchor to be received within said distal end of said axial passageway, and (ii) a second extended position wherein said shaft's distal end surface projects out of said distal end of said axial passageway;

a peripheral rib formed on the exterior surface of said shaft housing;

rib engaging means disposed on a shaft handle connected to said shaft, for yieldably engaging said peripheral rib as said shaft moves from said first retracted position to said second extended position, whereby when said shaft is in said first retracted position, the interaction of said peripheral rib and said rib engaging means prevents said shaft from moving into said second extended position until a sufficient distally-directed force is applied to said shaft to cause said rib engaging means to override said peripheral rib; and suture management means for managing a free end of a suture attached to said suture anchor when said suture anchor is disposed in said distal end of said axial passageway, said suture management means comprising a recess defining a first surface and an elastomer disposed in said recess so as to yieldably engage said first surface, whereby a free end of a suture may be forced between said first surface and said elastomer and retained there until thereafter forcibly withdrawn;

said shaft housing having an inwardly-directed protrusion therein engageable with notch and slide surfaces of said shaft to determine mobility of said shaft handle axially and rotatively on said shaft housing.

8. A method for deploying a bone anchor in bone, said method comprising the steps of:

(1) providing a system for deploying a suture anchor in a hole formed in a bone, said system comprising:

(i) a suture anchor comprising a generally cylindrical housing, a pair of flexible barbs extending laterally from said housing, and suture attachment means for attaching a length of suture to said housing; and (ii) an installation tool for deploying said suture anchor in the bone, said installation tool comprising:

a body comprising a sleeve, a sleeve handle fixed to said sleeve, and a shaft housing connectable to said sleeve handle, said body having a distal portion and a proximal portion, said distal portion terminating in a distal end surface of said sleeve and said proximal portion terminating in a proximal end surface of said shaft housing, and further wherein an axial passageway extends between said distal end surface and said proximal end surface, with said distal end of said axial passageway being sized to receive at least a portion of said suture anchor therein, and having therein an annular shoulder for seating a proximal end of said suture anchor;

a shaft slidably disposed in said axial passageway, said shaft terminating in a distal end surface and being adapted to move between (i) a first retracted position wherein said shaft's distal end surface is withdrawn sufficiently far into the interior of said axial passageway so as to allow at least a portion of said suture anchor to be received within said distal end of said axial passageway, and (ii) a second extended position wherein said shaft's distal end surface projects out of said distal end of said axial passageway;

a peripheral rib formed on the exterior surface of said shaft housing;

rib engaging means disposed on a shaft handle connected to said shaft for yieldably engaging said peripheral rib as said shaft moves from said first retracted position to said second extended position, whereby when said shaft is in said first retracted position, the interaction of said peripheral rib and said rib engaging means prevents said shaft from moving into said second extended position until a sufficient distally-directed force is applied to said shaft to cause said rib engaging means to override said peripheral rib; and suture management means for managing a free end of a suture attached to said suture anchor when said suture anchor is disposed in said distal end of said axial passageway, said suture management means comprising a recess defining a first surface and an elastomer disposed in said recess so as to yieldably engage said first surface, whereby a free end of a suture may be forced between said first surface and said elastomer and retained there until thereafter forcibly withdrawn;

said shaft housing having an inwardly-directed protrusion therein engageable with notch and slide surfaces of said shaft to determine mobility of said shaft handle axially and rotatively on said shaft housing;

(2) positioning said shaft in said first retracted position;

(3) positioning said suture anchor at least partially within said distal end of said axial passageway and on said sleeve annular shoulder, and positioning a free end of a suture attached to said suture anchor between said first surface and said elastomer;

(4) positioning said distal end of said installation tool against a top surface of the bone having the hole formed therein, with said suture anchor being aligned with the hole;

(5) moving said shaft from said first retracted position to said second extended position to deploy said suture anchor in the bone; and (6) removing said free end of said suture attached to said suture anchor from between said first surface and said elastomer.

* * * * *